United States Patent [19]

Krüger

[11] 4,259,502
[45] Mar. 31, 1981

[54] PROCESS FOR THE PREPARATION OF 5-MERCAPTO-1,2,3-TRIAZOLES

[75] Inventor: Hans-Rudolf Krüger, Berlin, Fed. Rep. of Germany

[73] Assignee: Schering Aktiengesellschaft, Berlin and Bergkamen, Fed. Rep. of Germany

[21] Appl. No.: 96,574

[22] Filed: Nov. 21, 1979

Related U.S. Application Data

[62] Division of Ser. No. 25,899, Apr. 2, 1979, Pat. No. 4,228,104.

[30] Foreign Application Priority Data

Nov. 29, 1978 [DE] Fed. Rep. of Germany ....... 2852067

[51] Int. Cl.³ ............................................ C07D 249/04
[52] U.S. Cl. .................................... 548/255; 548/127
[58] Field of Search .............................. 548/127, 255

[56] References Cited

U.S. PATENT DOCUMENTS

4,012,382  3/1977  Bouzard et al. ..................... 548/255

OTHER PUBLICATIONS

Goerdeler et al., Ber. Deut. Chem. Ges., vol. 99, pp. 1618–1631 (1966).
Smith, Open-chain Nitrogen Compounds, (W. A. Benjamin, Inc., New York, 1965), Vol. 1, pp. 71–72.
Smith, Open-chain Nitrogen Compounds, (W. A. Benjamin, Inc., New York, 1965), vol. 2, p. 219.
Wagner et al., Synthetic Organic Chemistry, (New York, 1953), p. 575.
Theilheimer, Synthetic Methods of Organic Chemistry, vol. 17, (New York, 1963), p. 215.

*Primary Examiner*—Alton D. Rollins
*Attorney, Agent, or Firm*—Michael J. Striker

[57] ABSTRACT

A process for the preparation of compound of the general formula

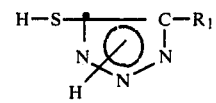

I described, in which a compound of formula

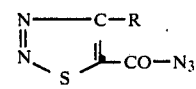

II is reacted with alcohol or phenol of formula $$H-O-R_2$$   III in an organic solvent to form a compound of formula

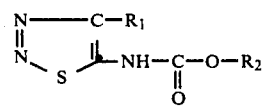

IV which is converted by acid or base catalyzed reaction to form a compound of formula

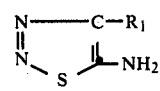

V which is then rearranged in the presence of base to form the desired product.

8 Claims, No Drawings

PROCESS FOR THE PREPARATION OF 5-MERCAPTO-1,2,3-TRIAZOLES

The invention concerns a novel process for the preparation of 5-mercapto-1,2,3-triazoles, which are useful for the preparation of plant protection products as well as pharmaceuticals.

A process for the preparation of 5-mercapto-1,2,3-triazoles is already known (J. Goerdeler and G. Gnad, Chem. Ber. 99, 1618 (1966)). This process has the great disadvantage that is employs 5-amino-1,2,3-thiadiazole as starting material, a substance with is neither easily prepared nor totally safe.

It is therefore an object of the invention to provide a process which allows for a problem-free preparation of 5-mercapto-1,2,3-triazoles in a limited number of steps and good yield, and which would make possible a technical preparation of this substance class without the isolation of certain somewhat unsafe intermediates.

This object is achieved through a process for the preparation of 5-mercapto-1,2,3-triazoles of the general formula

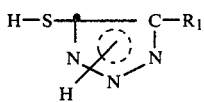

in which $R_1$ is hydrogen or an optionally substituted $C_1$–$C_4$ carbon residue, and which may be characterized, in that one dissolves a 1,2,3-thiadiazol-5-carboxylic acid azide of the formula

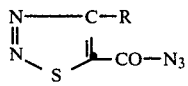

and an alcohol or phenol of the general formula

in an inert organic solvent, to react to form a (1,2,3-thiadiazol-5-yl)-carbaminic acid ester of the general formula

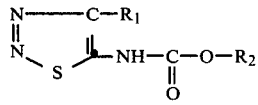

which is then converted through an acid- or base-catalyzed reaction to form 5-amino-1,2,3-thiadiazole of the general formula

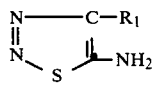

which is rearranged in the presence of bases and the reaction product isolated in known manner. In the above formulas, $R_2$ is an optionally substituted $C_1$–$C_4$ alkyl residue, an optionally substituted $C_5$–$C_8$ cycloalkyl residue, and optionally substituted aryl-$C_1$–$C_3$ alkyl residue or an aromatic hydrocarbon residue optionally substituted in one or more position by one or more moieties selected from the group consisting of $C_1$–$C_6$ alkyl, $C_1$–$C_6$ alkoxy, halogen, nitro and trifluoromethyl.

Examples of $R_1$ in the general formula I include hydrogen, methyl, ethyl, propyl, isopropyl, butyl, sec-butyl, isobutyl, t-butyl, chloromethyl, methylthiomethyl, and hydroxymethyl.

As examples of residues within the scope of $R_2$, the following may be mentioned: alkyl of 1 to 4 carbons, such as methyl, ethyl, propyl, isopropyl, butyl, sec-butyl, isobutyl, t-butyl; $C_5$–$C_8$ cycloalkyl such as cyclopentyl, cyclohexyl, 2-methylcyclohexyl, 3-methylcyclohexyl, 4-methylcyclohexyl, cycloheptyl, cyclooctyl; aryl-$C_1$–$C_3$-alkyl such as benzyl, 4-chlorobenzyl, 2-chlorobenzyl, 4-methylbenzyl, 3-methylbenzyl, 2,4-dichlorobenzyl, 3,4-dichlorobenzyl, 4-methoxybenzyl, α,α-dimethylbenzyl, 1-phenylethyl, 2-phenylethyl, 3-phenylpropyl, 2-phenylpropyl, 1-phenylpropyl; aromatic and substituted aromatic hydrocarbons such as phenyl, 4-chlorophenyl, 3-chlorophenyl, 2-chlorophenyl, 2,4-dichlorophenyl, 3,4-dichlorophenyl, pentachlorophenyl, 4-fluorophenyl, 4-methylphenyl, 3-methylphenyl, 2-methylphenyl, 4-nitrophenyl, 3-trifluoromethylphenyl, 4methoxyphenyl, and 3-methoxyphenyl.

Particular embodiments of the inventive process include the following:

(1) The reaction of the 1,2,3-thiadiazol-5-carboxylic acid azide of formula II with alcohol or phenol of formula III takes place at temperatures between about 20° and 180° C., preferably between 50° and 120° C. The reaction may be carried out at the boiling point of the reaction mixture. Equimolar amounts of the azide of formula II and the alcohol or phenol of formula III are reacted together; the reaction of the azide of formula II with the alcohol or phenol of formula III is carried out in a single step. The reaction may be carried out with 1,2,3-thiadiazol-5-carboxylic acid azide of formula II which is prepared according to known methods and not isolated out of the reaction mixture in which it is formed, which makes possible a continuous process.

(2) A (1,2,3-thiadiazol-5-yl)carbaminic acid ester of general formula IV may be used, which is not isolated from the reaction mixture, and the compound of formula IV, in an acid- or base-catalyzed reaction at temperatures between about 0° and 150° C. preferably between 50° and 120° C., is converted to 5-amino-1,2,3-thiadiazole of formula V, which is not isolated from the solution in which it is generated.

(3) The 5-amino-1,2,3-thiadiazole of formula V is not isolated from the reaction mixture in which it is prepared, and is reacted in known manner at temperatures between about 0° and 150° C., preferably 50° and 120° C., in the presence of base to form 5-mercapto-1,2,3-triazoles of general formula I.

The 1,2,3-thiadiazol-5-carboxylic acid azide of formula II can be prepared according to known methods, in which for example (a) 1,2,3-thiadiazol-5-carboxylic acid of formula

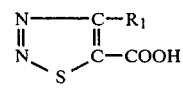

with chloroformic acid esters of formula

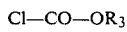

forms, in an inert organic solvent in the presence of acid-binding agents, the mixed anhydride of the general formula

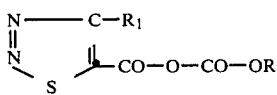   VIII which is then reacted with a solution of alkali azide of the general formula MeN$_3$   IX (b) 1,2,3-thiadiazol-5-carboxylic acid halide of general formula

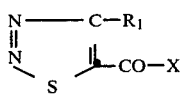   X is reacted with an aqueous solution of alkali azide of general formula MeN$_3$   IX in inert organic solvents, or (c) 1,2,3-thiadiazol-5-carboxylic acid hydrozide of formula

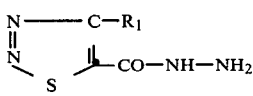   XI is reacted in inert solvent with solutions of alkali nitrites of general formula MeNO$_2$   XII or with alkyl nitrites of general formula

R$_3$—O—NO in the presence of acid to form 1,2,3-thiadiazol-5-carboxylic acid azides of formula II. In the above, R$_3$ is a C$_1$–C$_6$ alkyl residue, Me a univalent metal equivalent, preferably sodium, potassium or lithium, and X halogen, preferably chlorine.

The inventive process provides for the preparation of the products from easily accessible starting materials, and makes possible a technically simple and safe preparation of the desired products.

It is of great technical advantage, that neither the 1,2,3thiadiazol-5-carboxylic acid azide of formula II nor the Curtius degradation intermediate 1,2,3-thiadiazol-5-yl isocyanate need be isolated from the reaction mixture in which they are generated. In fact, the carboxylic acid azide II can be directly combined with the alcohol or phenol III in a single pot reaction.

It is further an advantage that the unpurified (1,2,3-thiadiazol-5-yl)-carbaminic acid ester IV as well as its raw solution or suspension can be used directly. In particular, in this manner the not entirely safe 5-amino-1,2,3-thiadiazole of formula V produced in the final carbamate hydrolysis is as a rule formed only in situ and then only in solution, and is not isolated; it reacts spontaneously with the alkali to form 5-mercapto-1,2,3-triazole of formula I by rearrangement.

It is particularly surprising that through suitable choice of the residue R$_2$ the carbamate hydrolysis can be carried out both with acid and with base, as on the one hand carbamates of formula IV from very stable salts with inorganic bases, while on the other hand the 5-amino-1,2,3-thiadiazole V has been described as unstable in the presence of acids.

The reaction of 1,2,3-thiadiazole-5-carboxylic acid azide of formula II, preferably in the form of the raw solution, to form (1,2,3-thiadiazole-5-yl)-carbaminic acid esters of formula IV occurs through a Curtius degradation via the 1,2,3-thiadiazol-5-yl isocyanate intermediate, which in any event as a rule is not separately isolated, but instead is generated in situ and reacted immediately with the alcohol or phenol of formula III.

This reaction may be carried out at temperatures between 20° and 180° C., preferably between 50° and 120° C., and most preferably at the reflux temperature of the corresponding solvent. It is advantageous in praxi if equimolar amounts of the raw solution of the azide and the alcohol or phenol are allowed to drop on their own in an inert solvent at the reflux temperature thereof, or else to introduce the azide solution into a solution of the alcohol or phenol thinned with solvent at the reflux temperature of the mixture.

The intensity of the reflux provides a possibility for control of the spontaneous course of the reaction.

The azide can also be heated in the presence of an inert solvent in a mixture with the alcohol or phenol. In contrast, the known method for carrying out the Curtius degradation— namely, first forming the isocyanate and then adding the alcohol or pehnol—has no advantage on account of the low yields.

As solvents inert with respect to the reactants, the following may be mentioned: aliphatic and aromatic hydrocarbons, such as cyclohexane, heptane, ligroin, benzene, chlorobenzene, toluene and xylene; ethers such as dioxane, tetrahydrofuran and diisopropylether, esters such as ethyl acetate and malonic ester, ketones such as acetone, methyl isobutyl ketone, isophorone, cyclohexanone; halogenated hydrocarbons such as methylene chloride, chloroform, carbon tetrachloride and 1,2-dichloroethane; and carboxylic acid nitriles such as acetonitrile. After the reaction the raw solution or suspension can be used directly, or if a further purification is desired, this can be carried out in conventional manner, such as for example by distilling off and added solvent at normal or reduced pressure, by precipitation with water or in the majority of cases through simple filtration of the desired product.

One obtains in this manner (1,2,3-thiadiazol-5-yl)-carbaminic acid esters in exceptionally pure form and in nearly quantitative yields, and which require for further application no additional purification operations.

If one continues to work with the raw solution or suspension, a solvent should be used for the Curtius degradation which is also inert during the following steps. As examples may be mentioned aromatic hydrocarbons such as benzene, toluene, xylene, chlorobenzene; ethers such as tetrahydrofuran and dioxan; and halogenated hydrocarbons such as chloroform, 1,2-dichloroethane and methylene chloride.

The saponification of (1,2,3-thiadiazol-5-yl)-carbaminic acid esters can be carried out in conventional manner with acid catalysis. In this method, it is also possible to isolate the 5-amino-1,2,3-thiadiazole.

The carbamate of formula IV, preferably in an aqueous medium, and if desired in a mixture with organic solvents, is heated in the presence of a acid catalyst. The reaction is carried out at temperatures between 0° C. and 150° C., preferably between 50° and 120° C. As suitable acid catalysts, the following may be mentioned: sulfuric acid, hydrochloric and hydrobromic acids, and p-toluene sulfonic acid. Solvents inert with respect to the reactants include halogenated hydrocarbons, such as methylene chloride, chloroform, 1,2-dichloroethane and carbon tetrachloride; aliphatic and aromatic hydrocarbons such as petrol, pentane, heptane, cyclohexane, benzene, toluene, xylene, chlorobenzene; and ethers such as diethyl ether, tetrahydrofuran and dioxane. Of particular significance is the use of carbamates of tertiary alcohols on account of the easy acid deesterification possible, with together with the facile dehydration of these alcohols leads to olefins.

It is advantageous to heat the toluene solution or suspension of t-butylester in the presence of p-toluene sulfonic acid, sulfuric acid or hydrochloric acid, which leads to the release of isobutylene and after decarboxylation to the corresponding 5-amino-1,2,3-thiadiazole of formula V. The product formed in the acidic aqueous medium in dissolved form is then in known manner, in the presence of a high concentration of inorganic bases such as oxides, hydroxides and carbonates of alkali or earth alkali metals as well as their alcoholates, reacted to form the 5-mercapto-1,2,3-triazole of formula I in the course of a Dimroth rearrangement. Through the use of high concentrations of base, the 5-mercapto-1,2,3-triazol is present in the form of the corresponding alkali or earth alkali salt, which is liberated only through the use of a suitable mineral acid. It is advantageous to use the base and 5-amino-1,2,3-thiadiazole of formula V in a 2:1 molar ratio.

The organic solvent used in the course of the reaction can also serve as extraction medium for the 5-mercapto-1,2,3-triazole.

After the subsequent reaction the extract is worked up in conventional manner, for example after corresponding drying through distilling off the added solvent at normal or reduced pressure.

One obtains in this manner 5-mercapto-1,2-triazoles in exceptionally pure form and in high yields. The reaction time, according to the temperature, can range between about 0.5 and 5 hours.

The saponification of the (1,2,3-thiadiazol-5-yl)-carbaminic acid ester can also be carried out under alkaline conditions. In this instance, the carbamate of formula IV, preferably in the form of the raw solution or suspension, is heated with an aqueous or alcoholic solution of alkali or earth alkali hydroxides in a molar ratio of about 1:3 (carbamate:base). The reaction is carried out at temperatures between about 0° and 150° C., preferably between about 50° and 120° C. The reaction time, depending upon the temperature, can range between about 0.5 and 15 hours.

In this form of the process, it is not possible to isolate the corresponding 5-amino-1,2,3-thiadiazole; instead, one obtains directly the alkali or earth alkali salt of the Dimroth rearrangement product. The 5-mercapto-1,2,3-triazole is obtained through conventional methods.

The invention may be better understood through the following examples.

EXAMPLE 1

Preparation of 5-mercapto-4-methyl-1,2,3-triazole In a 2 l round bottom flask with stirrer, thermometer and dropping funnel, 47.4 g (0.3 Mol) 4-methyl-1,2,3-thiadiazol-5-carboxylic acid hydrazide is dissolved in 300 ml water and 36 ml conc. hydrochloric acid. This solution is then mixed with 600 ml toluene. To this mixture, over 30 minutes at 0° to 5° a solution of 21.75 g (0.315) sodium nitrite in 60 ml water is added dropwise. It is stirred for about 15 minutes at 0° to 5° C., the toluene phase is separated off, washed with 150 ml ice water and dried over magnesium sulfate.

In a three-neck 2 l round bottom flask with stirrer, thermometer, reflux condenser and drying tube, about 150 ml toluene and 31.8 ml (0.33 Mol) t-butanol is heated to 90° C. The dried carboxylic acid axide solution is added dropwise over 20 minutes at such a rate, that an interior temperature between 100° and 110° C. is maintained. The mixture is stirred for 30 minutes at 100° to 110° C., cooled to 5° C. and the crystals recovered and dried to constant weight at 40° C. under vacuum.

Yield: 47.1 g = 73% of theory M.P.: 152°–153° C. (decomp.) TLC: Solvent: ethyl acetate $R_f$: 0.545

4-methyl-1,2,3-thiadiazol-5-yl)-carbaminic acid-t-butyl ester

In a three-neck 1 l round bottom flask with stirrer, thermometer and reflux condenser 21.5 g (0.1 Mol) (4-methyl-1,2,3-thiadiazol-5-yl)-carbaminic acid t-butyl ester is warmed to 80° C. with vigorous stirring in a mixture of 250 ml toluene and 200 ml water, and then reacted over 15 minutes with 8 ml concentrated hydrochloric acid. The mixture is stirred for 15 minutes at 80° C., cooled to 20° C., reacted with a solution of 12 g (0.3 Mol) sodium hydroxide in 50 ml water and then warmed for 5 minutes to 80° C. The mixture is then cooled to 20° C., the toluene phase separated off and discarded; the aqueous phase is acidified with 20 ml concentrted hydrochloric acid, mixed with 75 g salt and extracted with ethyl acetate. The ethyl acetate extract after drying over magnesium sulfate is concentrated to dryness at 40° C. under vacuum.

One obtains light yellow crystals.

5-mercapto-4-methyl-1,2,3-triazole

Yield: 6.0 g = 52.1% of theory M.P.: 100°–105° C.

EXAMPLE 2

Preparation of 5-mercapto-1,2,3-triazole

In an analogous manner to Example 1,(1,2,3-thiadiazol-5-yl)-carbaminic acid phenyl ester, with M.P. = 216° C. (decomp.) is prepared from 1,2,3-thiadiazol-5-carboxylic acid hydrazide in a yield of 88.1% of theory.

In a three-neck 500 ml round bottom flash with stirrer, thermometer and reflux condenser, 44.25 g (0.2 Mol)(1,2,3-thiadiazol-5-yl)-carbaminic acid phenyl ester in a solution of 12 g (0.3 Mol) sodium hydroxide in 150 ml water is warmed to 95° C. for four hours. The solution is then cooled to 20° C. and combined with 26.4 ml conc. hydrochloric acid. After saturation with 100 g salt, the mixture is extracted with 150 ml ethyl acetate in portions; the extracts are then combined and shaken with a solution of 20 g potassium bicarbonate in 75 ml water. The aqueous phase is neutralized with 17.6 ml conc. hydrochloric acid and then extracted again with 150 ml ethyl acetate. The combined extracts after drying over magnesium sulfate are concentrated to dryness at 40° C. under vacuum. One obtains light yellow crystals.

Yield: 10.7 g=52.9% of theory M.P.: 53°–54° C.

EXAMPLE 3

Preparation of 5-mercapto-4-methyl-1,2,3-triazole

In a three-neck I l round bottom flask with stirrer, thermometer and dropping funnel, 31.6 g (0.2 Mol) 4-methyl-1,2,3-thiadiazol-5-carboxylic aicd hydrazide is dissolved in 200 ml water and 24 ml conc. hydrochloric acid. This solution is then mixed with 400 ml toluene. To this mixture over 15 minutes at 0°–5° C., a solution of 14.5 g (0.21 Mol) sodium nitrite in 40 ml water is added dropwise. This is stirred for 15 minutes at 0°–5° C., the toluene phase is separated off, washed with 100 ml water and dried over magnesium sulfate.

In a three-neck I l round bottom flask with stirrer, theremometer, reflux condenser, dropping funnel and drying tube, about 18.8 g (0.2 Mol) phenol in 100 ml toluene is heated to about 110° C. The dried carboxylic acid azide solution is added dropwise over 20 minutes at such a rate, that the internal temperature remains at 110°–110° C. This is stirred an additional 15 minutes at 100°–110° C., cooled at 90° C., the suspension mixed with a solution of 24 g (0.6 Mol) sodium hydroxide in 200 ml water and heated an additional 1.5 hours under reflux. The mixture is then cooled to 20° C., the aqueous phase separated off and mixed with 52.9 ml conc. hydrochloric acid. After saturation with 70 g salt, the mixture is extracted with 300 ml ethyl acetate in portions; the extracts are then shaken with a solution of 22 g potassium bicarbonate in 85 ml water.

The aqueous phase is finally mixed with 17.6 ml conc. hydrochloric acid and extracted in portions with 300 ml ethyl acetate. The collected extract dried over magnesium sulfate is evaporated to dryness at 40° C. under vacuum.

One obtains white crystals.

Yield: 12.9 g=56% of theory M.P.: 113°–114° C.

The products prepared according to the invention can be used an materials for the preparation of antibiotics, in particular cephalosporin derivatives.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A process for the preparation of 5-mercapto-1,2,3-triazoles of the general formula

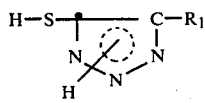   I wherein $R_1$ is hydrogen, a $C_1$–$C_4$ carbon residue or a substituted $C_1$–$C_4$ carbon residue, comprising reacting a compound of the formula

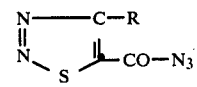   II in a single step with an alcohol or phenol of the formula $$H-O-R_2$$   III in an organic solvent to form a compound of the formula

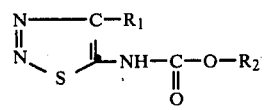   IV converting this compound through an acid or base catalyzed reaction to form a compound of the formula

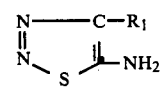   V rearranging this compound in the presence of base to form the product; and isolating the reaction product in conventional manner, wherein $R_1$ is hydrogen, methyl, ethyl, propyl, isopropyl, butyl, secbutyl, isobutyl, t-butyl, chloromethyl, methylthiomethyl or hydroxymethyl and $R_2$ is a $C_1$–$C_4$ alkyl residue, a substituted $C_1$–$C_4$ alkyl residue, a $C_5$–$C_8$ cycloalkyl residue, a substituted $C_5$–$C_8$ cycloalkyl residue, an aryl-$C_1$–$C_3$-alkyl residue, a substituted aryl-$C_1$–$C_3$-alkyl residue, an aromatic hydrocarbon residue, a substituted aromatic hydrocarbon residue substituted in one or more positions by one or more residues selected from the group consisting of $C_1$–$C_6$ alkyl, $C_1$–$C_6$ alkoxy, halogen, nitro and trifluoromethyl.

2. A process as defined in claim 1 wherein said reaction of compounds II and III takes place at a temperature between 50° and 120° C.

3. A process as defined in claim 1, wherein equimolar amounts of compounds II and III are reacted together.

4. A process as defined in claim 1, wherein a (1,2,3-thiadiazol-5-yl)-carbaminic acid ester is used which is not isolated from the reaction mixture.

5. A process as defined in claim 1, wherein a carbaminic acid ester of formula IV is converted to a compound of general formula V which is not isolated from the reaction mixture, in a base or acid catalyzed reaction at temperatures between about 0° and 150° C.

6. A process as defined in claim 1, wherein compound V is employed in raw form not isolated from the reaction mixture in which it is generated.

7. A process as defined in claim 1, wherein a compound of formula V is rearranged to form a compound I in known manner at temperatures between about 0° and 150° C., in the presence of bases.

8. A process as defined in claim 7, at temperatures between 50° and 120° C.

* * * * *